US010538684B2

(12) United States Patent
Spyrou et al.

(10) Patent No.: US 10,538,684 B2
(45) Date of Patent: *Jan. 21, 2020

(54) COATING COMPOSITIONS COMPRISING MONOALLOPHANATES BASED ON ALKOXYSILANE ALKYL ISOCYANATES

(71) Applicant: Evonik Operations GmbH, Essen (DE)

(72) Inventors: Emmanouil Spyrou, Schermbeck (DE); Tobias Unkelhaeusser, Duelmen (DE); Sabine Naumann, Herne (DE); Manfred Kreczinski, Herne (DE); Holger Loesch, Herne (DE); Alina Meier, Marl (DE); Uwe Korek, Duelmen (DE)

(73) Assignee: Evonik Operations GmbH, Essen (DE)

( * ) Notice: Subject to any disclaimer, the term of this patent is extended or adjusted under 35 U.S.C. 154(b) by 43 days.

This patent is subject to a terminal disclaimer.

(21) Appl. No.: 15/770,733

(22) PCT Filed: Oct. 7, 2016

(86) PCT No.: PCT/EP2016/073976
§ 371 (c)(1),
(2) Date: Apr. 24, 2018

(87) PCT Pub. No.: WO2017/071933
PCT Pub. Date: May 4, 2017

(65) Prior Publication Data
US 2018/0312713 A1  Nov. 1, 2018

(30) Foreign Application Priority Data

Oct. 29, 2015  (EP) .................... 15192087

(51) Int. Cl.
| C09D 133/14 | (2006.01) |
| C09D 175/04 | (2006.01) |
| C08G 18/62 | (2006.01) |
| C08G 18/38 | (2006.01) |
| C08G 18/71 | (2006.01) |
| C07F 7/18 | (2006.01) |
| C08L 75/04 | (2006.01) |

(52) U.S. Cl.
CPC .......... *C09D 133/14* (2013.01); *C07F 7/1892* (2013.01); *C08G 18/3893* (2013.01); *C08G 18/6225* (2013.01); *C08G 18/718* (2013.01); *C08L 75/04* (2013.01); *C09D 175/04* (2013.01)

(58) Field of Classification Search
None
See application file for complete search history.

(56) References Cited

U.S. PATENT DOCUMENTS

| 4,772,672 A | 9/1988 | Isozaki et al. |
| 5,516,559 A | 5/1996 | Röckrath et al. |
| 7,812,087 B2* | 10/2010 | Ludewig ............... C08G 18/10 |
| | | 524/589 |
| 10,351,579 B2* | 7/2019 | Spyrou ................. C08F 20/00 |
| 2007/0055010 A1 | 3/2007 | Ludewig et al. |
| 2007/0055035 A1 | 3/2007 | Ludewig et al. |
| 2008/0245999 A1 | 10/2008 | Poppe et al. |
| 2008/0255354 A1* | 10/2008 | Popp ..................... C07F 7/1892 |
| | | 544/221 |
| 2009/0326146 A1 | 12/2009 | Sepeur et al. |
| 2010/0010113 A1 | 1/2010 | Schwalm et al. |
| 2010/0098950 A1 | 4/2010 | Gruber et al. |

(Continued)

FOREIGN PATENT DOCUMENTS

| DE | 10 2005 041 953 | 3/2007 |
| DE | 10 2005 041 954 | 3/2007 |

(Continued)

OTHER PUBLICATIONS

International Search Report mailed in PCT/EP2016/073976 dated Nov. 28, 2016, with English translation.

(Continued)

Primary Examiner — Satya B Sastri
(74) Attorney, Agent, or Firm — Grüneberg and Myers PLLC

(57) ABSTRACT

A coating composition that includes an allophanate-containing compound can offer improved scratch resistance. The coating composition includes A) at least one allophanate-containing compound having the formula (1):

$$R_n(R^1O)_{3-n}Si \overset{R^2}{\underset{}{-}} N \overset{O}{\underset{}{-}} \underset{OR^3}{\overset{}{-}} \\ O \overset{}{-} \underset{H}{N} \overset{R^4}{\underset{}{-}} Si(R^5O)_{3-m}R_m^6,$$ (1)

wherein R, $R^1$-$R^6$ are each independently identical or different hydrocarbyl radicals having 1-8 carbon atoms, which may be branched or cyclic, or else may be integrated together to form a cyclic system, and m and n are each independently 0-2, B) a binder, C) optionally, an aliphatic or cycloaliphatic polyisocyanate having an NCO functionality of at least 2, D) optionally, a catalyst, E) optionally, an auxiliary and/or additive, and, F) optionally, a solvent.

17 Claims, No Drawings

(56) References Cited

U.S. PATENT DOCUMENTS

| | | | |
|---|---|---|---|
| 2011/0045190 | A1 | 2/2011 | Groenewolt et al. |
| 2011/0065957 | A1 | 3/2011 | Bernard et al. |
| 2014/0097392 | A1 | 4/2014 | Berge et al. |
| 2016/0194341 | A1* | 7/2016 | Haaf-Kleinhubbert ........................ C08G 18/6715 524/869 |
| 2017/0369626 | A1 | 6/2017 | Stache |
| 2017/0369631 | A1 | 6/2017 | Stache |
| 2017/0369736 | A1 | 6/2017 | Stache |
| 2017/0369627 | A1 | 12/2017 | Stache et al. |

FOREIGN PATENT DOCUMENTS

| | | |
|---|---|---|
| DE | 10 2005 045 228 | 4/2007 |
| EP | 1 204 701 | 9/2005 |
| WO | 1992/011328 | 7/1992 |
| WO | 1993/015849 | 8/1993 |
| WO | 2008/043722 | 4/2008 |
| WO | 2008/043723 | 4/2008 |
| WO | 2008/131715 | 11/2008 |
| WO | 2017/071941 | 5/2017 |

OTHER PUBLICATIONS

Written Opinion of the International Searching Authority mailed in PCT/EP2016/073976 dated Nov. 28, 2016.

* cited by examiner

COATING COMPOSITIONS COMPRISING MONOALLOPHANATES BASED ON ALKOXYSILANE ALKYL ISOCYANATES

This application is a National Stage entry under § 371 of International Application No. PCT/EP2016/073976, filed on Oct. 7, 2016, and which claims priority to European Patent Application No. 15192087.3, filed on Oct. 29, 2015.

The invention relates to coating compositions comprising novel monoallophanates based on alkoxysilane alkyl isocyanates, to a process for preparation and to use.

Polyurethanes have been established for many decades as high-value components for paint, adhesive, sealant and plastics systems. It is possible here for additional alkoxysilane groups to play an important role, for example with regard to network density, chemical resistance and scratch resistance, primarily through the formation of siloxane structures. Systems of this kind are also known.

Molecules both possessing alkoxysilane groups and having isocyanate groups offer the option of introducing both the functionalities mentioned, siloxanes and polyurethane groups, by means of one component. Such substances too have long been in use, for example isocyanatoalkyltrialkoxysilanes. It is possible to use these substances, by reaction with polyalcohols, to prepare isocyanate-free moisture-curing crosslinkers.

In principle, such "SiPURs" (alkoxysilane-containing polyurethanes) can be reacted with further isocyanates to give allophanates, in order to modify particular material properties, for example viscosity.

For instance, DE102005041953A1 describes a reaction of a polyol having a mean molecular weight of 3000-20,000 g/mol with an excess of isocyanatopropyltrimethoxysilane, so as to result in an allophanate reaction after the polyurethane formation.

In DE102005041954A1, a polyurethane formed from a polyol and a diisocyanate (e.g. IPDI, isophorone diisocyanate) is admixed with isocyanatopropyltrimethoxysilane and heated until allophanate structures form.

EP2089444A1 claims allophanate-containing polyurethanes which, as well as an unsaturated functionality, also have silane-containing components.

The situation is similar in EP2089445A1; here, however, these polyurethanes additionally have to contain a dispersion-active component in order to make them water-compatible.

US20140097392A1 also discusses allophanate- and alkoxysilane-containing polymers, which in this case are blended with a dye.

J. Kozakiewicz et al. published, in *Progress in Organic Coatings* 72 (2011) 120-130, silane-containing blocking agents for polyisocyanates which have been introduced via an allophanate group.

There is obviously a need for further compounds bearing alkoxysilane groups, particularly for scratch-resistant applications. However, it is common to all the existing examples that they are always polymers and/or polyurethanes which both have high viscosities and are difficult to purify or to isolate.

The problem addressed by this invention was that of making available coating compositions comprising novel alkoxysilane-bearing compounds having scratch-resistant properties, which do not have the disadvantage of the prior art, but are especially easy to prepare, have low viscosities and can be purified with a low level of complexity.

It has been found that, surprisingly, monoallophanates consisting of an isocyanate-modified alkoxysilane-containing monourethane have the desired properties.

The invention provides a
coating composition comprising
A) at least one allophanate-containing compound having the formula 1:

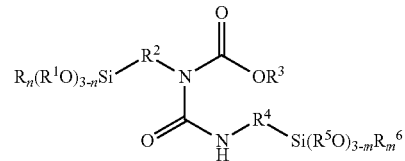

where R, $R^1$-$R^6$ are each independently identical or different hydrocarbyl radicals having 1-8 carbon atoms, which may be branched or cyclic, or else may be integrated together to form a cyclic system, and m and n are each independently 0-2, B) at least one binder, preferably a hydroxyl-containing binder, C) optionally at least one aliphatic or cycloaliphatic polyisocyanate having an NCO functionality of at least 2, preferably 2.8 to 6.

D) optionally at least one catalyst,

E) optionally auxiliaries and/or additive.

F) optionally solvents.

Preferably, m and n are each 0.

$R^1$ and $R^5$ are each independently preferably methyl or ethyl.

$R^2$ and $R^4$ are each independently preferably methyl or propyl.

More preferably, $R^1$=$R^5$ and $R^2$=$R^4$.

Preference is given to compounds where m and n are each 0, $R^1$ and $R^5$ are each methyl or ethyl, and $R^2$ and $R^4$ are each methyl or propyl.

Very particular preference is given to the compound where m and n are each 0, $R^1$=$R^5$=methyl and $R^2$=$R^4$=propyl.

The monoallophanates having the formula 1:

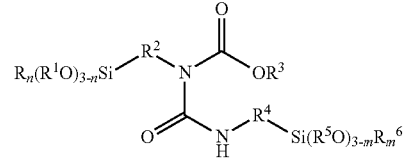

where R, $R^1$-$R^6$ are each independently identical or different hydrocarbyl radicals having 1-8 carbon atoms, which may be branched or cyclic, or else may be integrated together to form a cyclic system, and m and n are each independently 0-2, are prepared by reaction of A) with B):

Alkoxysilane-containing isocyanates A) have the formula 2:

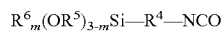

$R^6{}_m(OR^5)_{3-m}Si-R^4-NCO$ where $R^6$, $R^5$ and $R^4$ are each independently identical or different hydrocarbyl radicals having 1-8 carbon atoms, which may be branched or cyclic, or else may be integrated together to form a cyclic system, and m is 0-2.

Preferably, m=0.

$R^4$ is preferably methyl or propyl.

$R^5$ is preferably methyl or ethyl,

Preference is given to compounds where m is 0 and $R^4$ is methyl or propyl, and $R^5$ is methyl or ethyl.

Particular preference is given to isocyanatopropyltrimethoxysilane.

Alkoxysilane-containing monourethanes B) have the formula 3:

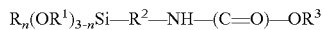

$$R_n(OR^1)_{3-n}Si-R^2-NH-(C=O)-OR^3$$

where R, $R^1$, $R^2$ and $R^3$ are each independently identical or different hydrocarbyl radicals having 1-8 carbon atoms, which may be branched or cyclic, or else may be integrated together to form a cyclic system, and n is 0-2.

Preferably, n=0.

$R^1$ is preferably methyl or ethyl.

$R^2$ is preferably methyl or propyl.

Preferably, $R^3=R^1$.

Preference is given to compounds where n is 0 and $R^2$ is methyl or propyl, and $R^1$ is methyl or ethyl and $R^3=R^1$.

Particular preference is given to N-trimethoxysilylpropylmethyl carbamate.

The monoallophanates are generally prepared solventlessly or using non-protic solvents, and the reaction may take place batchwise or continuously. The reaction is conducted in suitable equipment, for example stirred tanks, extruders, static mixers, kneading chambers. The reaction may be operated at room temperature, in other words at temperatures in the range from 20 to 22° C., though preferably higher temperatures are used, in the range from 80 to 220° C., more particularly in the range from 80 to 120° C. To accelerate the reaction, it is advantageously possible to use catalysts known in urethane chemistry, for example organometallic compounds such as tin or zinc compounds, salts, for example Zn(II) chloride, and/or bases. Suitable examples are carboxylates of Sn, Bi, Zn and other metals, for example dibutyltin dilaurate, tin octoate, bismuth neodecanoate, tert-amines, for example 1,4-diazabicyclo[2.2.2]octane (DABCO), triethylamine, amidines and guanidines, quaternary ammonium salts, preferably tetraalkylammonium salts, and/or quaternary phosphonium salts.

Useful catalysts include metal acetylacetonates. Examples thereof are zinc acetylacetonate, lithium acetylacetonate, iron acetylacetonate and tin acetylacetonate, alone or in mixtures. Preference is given to using zinc acetylacetonate. Useful catalysts are also quaternary ammonium acetylacetonates or quaternary phosphonium acetylacetonates. Preference is given to zinc ethylhexanoate. The reaction is conducted with exclusion of water. Preference is given to conducting the reaction solventlessly.

The coating composition of the invention consists preferably essentially of components A), B), C), D) and E). In one preferred embodiment this means that the sum of the components A), B), C), D) and E) in the sequence of increasing preference makes up at least 45, 50, 55, 60, 65, 70, 75, 80, 85, 90, 92, 94, 96, 98 or 99 weight percent of the coating composition.

In one preferred embodiment, the coating composition of the invention is a non-aqueous coating composition. In one particularly preferred embodiment, the term "non-aqueous", as used herein, means that the coating composition of the invention, based on the sum of the components A), B), C), D) and E), has a water fraction of not more than 3 weight percent, preferably not more than 1 weight percent. In a most preferred embodiment, the coating composition of the invention is free of water.

Component A) is included in the coating composition of the invention at 10 to 99 wt %, preferably at 10 to 70 wt %, based on the sum of the components A), B) and C).

The aliphatic or cycloaliphatic polyisocyanate C) used as crosslinker component comprises at least one aliphatic and/or cycloaliphatic polyisocyanate having an NCO functionality of at least 2, preferably 2 to 6, more preferably from 2.8 to 6, most preferably 2 to 4. In a preferred embodiment the term "NCO functionality" as used herein refers to the number of reactive NCO substituents possessed on average by the molecule in question, preferably the crosslinker component C).

The polyisocyanate used in accordance with the invention may be any aliphatic, cycloaliphatic and/or (cyclo)aliphatic diisocyanate. In one preferred embodiment the term "(cyclo)aliphatic diisocyanate" as used herein means that in a molecule there are present simultaneously NCO groups bonded to a ring and NCO groups bonded to an aliphatic radical, as is the case, for example, for isophorone diisocyanate. In one preferred embodiment the term "cycloaliphatic diisocyanate" as used herein refers to a diisocyanate which only has NCO groups bonded directly on the cycloaliphatic ring, an example being diisocyanatodicyclohexylmethane (H12MDI).

Aliphatic diisocyanates suitable for use as polyisocyanate C) include a linear or branched alkylene radical having preferably 3 to 16 carbon atoms, more preferably 4 to 12 carbon atoms. Suitable cycloaliphatic or (cyclo)aliphatic diisocyanates include a cycloalkylene radical having preferably 4 to 18 carbon atoms, more preferably 6 to 15 carbon atoms. Examples of suitable di- or polyisocyanates include cyclohexane diisocyanate, methylcyclohexane diisocyanate, ethylcyclohexane diisocyanate, propylcyclohexane diisocyanate, methyldiethylcyclohexane diisocyanate, propane diisocyanate, butane diisocyanate, pentane diisocyanate, hexane diisocyanate, heptane diisocyanate, octane diisocyanate, nonane diisocyanate, nonane triisocyanate, such as 4-isocyanatomethyl-1,8-octane diisocyanate (TIN), decane di- and triisocyanate, undecane di- and triisocyanate, dodecane di- and triisocyanates. Likewise suitable are 4-methylcyclohexane 1,3-diisocyanate, 2-butyl-2 ethylpentamethylene diisocyanate, 3(4)-isocyanatomethyl-1-methylcyclohexyl isocyanate, 2-isocyanatopropylcyclohexyl isocyanate, 2,4'-methylenebis(cyclohexyl) diisocyanate and/or 1,4-diisocyanato-4-methylpentane.

The diisocyanate used as polyisocyanate is preferably selected from the group comprising isophorone diisocyanate (IPDI), hexamethylene diisocyanate (HDI), diisocyanatodicyclohexylmethane (H12MDI), 2-methylpentane diisocyanate (MPDI), 2,2,4-trimethylhexamethylene diisocyanate/2,4,4-trimethylhexamethylene diisocyanate (TMDI), norbornane diisocyanate (NBDI). Particular preference is given to IPDI, HDI, TMDI and/or H12MDI, with IPDI, H12MDI and/or HDI representing the most preferred polyisocyanates.

Particular preference is given to using polyisocyanates which can be prepared from the stated diisocyanates or mixtures thereof by linking by means of urethane, allophanate, urea, biuret, uretdione, amide, isocyanurate, carbodiimide, uretonimine, oxadiazinetrione or iminooxadiazinedione structures. Such polyisocyanates are commercially available. Particularly suitable are isocyanurates, especially formed from IPDI and/or HDI, e.g. VESTANAT HT 2500 L and VESTANAT T 1890. Polyisocyanates of this kind can optionally additionally be chain-extended or branched with di- or polyfunctional H acidic components, for example di- or polyols and/or di- or polyamines. Those whose use is preferred in accordance with the invention are freed from residual monomers by distillative removal, so that the diisocyanate residual monomer content is <0.5 wt %.

For the purposes of the present invention, any desired mixtures of the above-described diisocyanates and/or polyisocyanates may be used.

Component C), if present, is included in the coating composition of the invention at 5 to 50 weight percent, preferably 15 to 40 weight percent, based on the sum of the components A), B) and C). For example, C), based on the sum of the components A), B) and C), is present at 50 weight percent in the coating composition of the invention if there are 25 g of A), 12.5 g of B) and 12.5 g of C). The amount of component C) in the coating composition of the invention is guided by the content of the groups chemically crosslinkable with polyisocyanates typically OH groups of component B). The molar ratio of the isocyanate groups of component C) to the OH groups of component B) is 0.3:1 to 2:1, preferably 0,5:1 to 1.5:1 and more preferably 0.7:1 to 1.3:1.

The coating composition of the invention comprises as component B) at least one binder. Suitable in principle as binders are all kinds of binders known to the skilled person, including, for example, binders which are thermoplastic, in other words not crosslinkable, which customarily have an average molecular weight >10 000 g/mol. Preferred binders, however, are those which possess reactive functional groups having acidic hydrogen atoms, examples being hydroxyl or primary or secondary amine groups. Suitable binders of the cited type have for example at least one, but preferably two or more, hydroxyl group(s). Further suitable functional groups of the binder are alkoxysilane functionalities, for example. Preference is given to using an adduct of an isocyanatotrialkoxysilane and a mono- or polyhydric alcohol, preferably adducts of 3-isocyanatopropyltrimethoxysilane, 3-isocyanatopropyltriethoxysilane, 3-isocyanatopropyltriisopropoxysilane, 2-isocyanatoethyltrimethoxysilane, 2-isocyanatoethyltriethoxysilane, 2-isocyanatoethyltriisopropoxysilane, 4-isocyanatobutyltrimethoxysilane, 4-isocyanatobutyltriethoxysilane, 4-isocyanatobutyltriisopropoxysilane, isocyanatomethyltrimethoxysilane, isocyanatomethyltriethoxysilane and/or isocyanatomethyltriisopropoxysilane.

As binders with functional groups, preference is given to using hydroxyl-containing polyesters, polyethers, polyacrylates, polycarbonates and polyurethanes having an OH number of 20 to 500 mg KOH/g and an average molar mass of 250 to 6000 g/mol. Particular preference in the context of the present invention is given to using hydroxyl-containing polyesters or polyacrylates having an OH number of 50 to 250 mg KOH/g and an average molecular weight of 500 to 6000 g/mol as binder components. The hydroxyl number (OH number, OHN) is determined in accordance with DIN 53240-2. This method comprises reacting the sample with acetic anhydride in the presence of 4-dimethylaminopyridine as catalyst to acetylate the hydroxyl groups. This affords one molecule of acetic acid per hydroxyl group while the subsequent hydrolysis of the excess acetic anhydride yields two molecules of acetic acid. The consumption of acetic acid is determined by titrimetry from the difference between the main value and a blank value to be carried out in parallel. The molecular weight is determined by means of gel permeation chromatography (GPC). The samples are characterized in tetrahydrofuran as eluent in accordance with DIN 55672-1, Hydroxyl-containing (meth)acrylic copolymers used as binder may be resins having a monomer composition of the kind described, for example, in WO 93/15849 (page 8, line 25 to page 10, line 5). In that case the acid number of the (meth)acrylic copolymer, to be set through proportional use of (meth)acrylic acid as monomer, ought to be 0 to 30, preferably 0 to 15 mg KOH/g. The number-average molar weight (determined by gel permeation chromatography against a polystyrene standard) of the (meth)acrylic copolymer is preferably 2000 to 20 000 g/mol; the glass transition temperature is preferably 40° C. to +60° C. The hydroxyl content of the (meth)acrylic copolymers for use in accordance with the invention, to be set through proportional use of hydroxyalkyl (meth)acrylates, is preferably 20 to 500 mg KOH/g, more preferably 50 to 250 mg KOH/g.

Polyester polyols suitable as binders in accordance with the invention are resins having a monomer composition composed of dicarboxylic and polycarboxylic acids and of dials and polyols, as described in WO 93/15849, Also employable as polyester polyols are polyaddition products of caprolactone onto low molecular weight di- and triols as are available under the trade name CAPA® (Perstorp) for example. The arithmetically determined number-average molar weight is preferably 500 to 5000 g/mol, more preferably 800 to 3000 g/mol; the average functionality is preferably 2.0 to 4,0, more preferably 2.0 to 3.5.

As urethane- and ester-group-containing polyols for use in accordance with the invention as binders, those employed include in principle those of the kind as described in EP 140 186. Preference is given to urethane- and ester-containing polyols which are prepared using HDI, IPDI, trimethylhexamethylene diisocyanate (TMDI) or dicyclohexylmethane diisocyanate (H12MDI). The number-average molar weight is preferably 500-5000 g/mol; the average functionality lies more particularly in the range of 2.0-3.5.

Trialkoxysilane-functional binders as well are suitable for use as component B). Such resins may be obtained by copolymerization of acrylate or methacrylate monomers with acryloyl- or methacryloyl-functional alkyl trialkoxysilane derivatives (for example Dynasylan® MEMO from Evonik Industries AG) as are described, for example, in WO 92/11328. An alternative synthesis comprises derivatization of hydroxyl group-containing polyethers, polyesters, polycarbonate dials or polyacrylates with isocyanatopropyltrialkoxysilane as is described, for example, in Examples 3 and 4 of WO2008/131715, Also useful are amino-containing binders, for example aminopropyltrimethoxysilane (e.g. Dynasylan AMMO from Evonik Industries AG), aminopropyltriethoxysilane, aminomethyltrimethoxysilane or aminomethyltriethoxysilane.

It will be appreciated that it is also possible to employ mixtures of the binders described hereinabove. Preferred binders are hydroxyl-containing polyesters and polyacrylates, alone or in mixtures.

The proportion of B) in the coating composition of the invention is preferably 1 to 90 weight percent, based on the sum of components A), B) and optionally C) and D), preferably 20 to 60 weight percent.

Catalyst D) is included in the coating composition of the invention, in one preferred embodiment, in an amount of 0.1 up to 5 weight percent, preferably 0.2 to 3 weight percent, based on the sum of the components A), B), optionally C) and D).

Catalysts D) used may be organic carboxylic acids. Examples of suitable carboxylic acids are, in particular, salicylic acid, benzoic acid, citric acid, phthalic acid, terephthalic acid, isophthalic acid, dodecanoic acid, 1,12-dodecanedioic acid and/or ascorbic acid. Preference is given to using salicylic acid, citric acid or benzoic acid, and mixtures of the stated carboxylic acids may also be employed.

Catalysts D) used are also quaternary ammonium salts alone or in mixtures, preferably tetraalkylammonium salts and/or quaternary phosphonium salts, with halogens, hydroxides, alkoxides or organic or inorganic acid anions as counterion. Examples of these are: tetramethylammonium formate, tetramethylammonium acetate, tetramethylammonium propionate, tetramethylammonium butyrate, tetramethylammonium benzoate, tetraethylammonium formate, tetraethylammonium acetate, tetraethylammonium propionate, tetraethylammonium butyrate, tetraethylammonium benzoate, tetrapropylammonium formate, tetrapropylammonium acetate, tetrapropylammonium propionate, tetrapropylammonium butyrate, tetrapropylammonium benzoate, tetrabutylammonium formate, tetrabutylammonium acetate, tetrabutylammonium propionate, tetrabutylammonium butyrate and tetrabutylammonium benzoate and tetrabutylphosphonium acetate, tetrabutylphosphonium formate and ethyltriphenylphosphonium acetate, tetrabutylphosphonium benzotriazolate, tetraphenylphosphonium phenoxide and trihexyltetradecylphosphonium decanoate, methyltributylammonium hydroxide, methyltriethylammonium hydroxide, tetramethylammonium hydroxide, tetraethylammonium hydroxide, tetrapropylammonium hydroxide, tetrabutylammonium hydroxide, tetrapentylammonium hydroxide, tetrahexylammonium hydroxide, tetraoctylammonium hydroxide, tetradecylammonium hydroxide, tetradecyltrihexylammonium hydroxide, tetraoctadecylammonium hydroxide, benzyltrimethylammonium hydroxide, benzyltriethylammonium hydroxide, trimethylphenylammonium hydroxide, triethylmethylammonium hydroxide, trimethylvinylammonium hydroxide, methyltributylammonium methoxide, methyltriethylammonium methoxide, tetramethylammonium methoxide, tetraethylammonium methoxide, tetrapropylammonium methoxide, tetrabutylammonium methoxide, tetrapentylammonium methoxide, tetrahexylammonium methoxide, tetraoctylammonium methoxide, tetradecylammonium methoxide, tetradecyltrihexylammonium methoxide, tetraoctadecylammonium methoxide, benzyltrimethylammonium methoxide, benzyltriethylammonium methoxide, trimethylphenylammonium methoxide, triethylmethylammonium methoxide, trimethylvinylammonium methoxide, methyltributylammonium ethoxide, methyltriethylammonium ethoxide, tetramethylammonium ethoxide, tetraethylammonium ethoxide, tetrapropylammonium ethoxide, tetrabutylammonium ethoxide, tetrapentylammonium ethoxide, tetrahexylammonium ethoxide, tetraoctylammonium methoxide, tetradecylammonium ethoxide, tetradecyltrihexylammonium ethoxide, tetraoctadecylammonium ethoxide, benzyltrimethylammonium ethoxide, benzyltriethylammonium ethoxide, trimethylphenylammonium ethoxide, triethylmethylammonium ethoxide, trimethylvinylammonium ethoxide, methyltributylammonium benzoxide, methyltriethylammonium benzoxide, tetramethylammonium benzoxide, tetraethylammonium benzoxide, tetrapropylammonium benzoxide, tetrabutylammonium benzoxide, tetrapentylammonium benzoxide, tetrahexylammonium benzoxide, tetraoctylammonium benzoxide, tetradecylammonium benzoxide, tetradecyltrihexylammoniumbenzoxide, tetraoctadecylammonium benzoxide, benzyltrimethylammonium benzoxide, benzyltriethylammonium benzoxide, trimethylphenylammonium benzoxide, triethylmethylammonium benzoxide, trimethylvinylammonium benzoxide, tetramethylammonium fluoride, tetraethylammonium fluoride, tetrabutylammonium fluoride, tetraoctylammonium fluoride, benzyltrimethylammonium fluoride, tetrabutylphosphonium hydroxide, tetrabutylphosphonium fluoride, tetrabutylammonium chloride, tetrabutylammonium bromide, tetrabutylammonium iodide, tetraethylammonium chloride, tetraethylammonium bromide, tetraethylammonium iodide, tetramethylammonium chloride, tetramethylammonium bromide, tetramethylammonium iodide, benzyltrimethylammonium chloride, benzyltriethylammonium chloride, benzyltripropylammonium chloride, benzyltributylammonium chloride, methyltributylammonium chloride, methyltripropylammonium chloride, methyltriethylammonium chloride, methyltriphenylammonium chloride, phenyltrimethylammonium chloride, benzyltrimethylammonium bromide, benzyltriethylammonium bromide, benzyltripropylammonium bromide, benzyltributylammonium bromide, methyltributylammonium bromide, methyltripropylammonium bromide, methyltriethylammonium bromide, methyltriphenylammonium bromide, phenyltrimethylammonium bromide, benzyltrimethylammonium iodide, benzyltriethylammonium iodide, benzyltripropylammonium iodide, benzyltributylammonium iodide, methyltributylammonium iodide, methyltripropylammonium iodide, methyltriethylammonium iodide, methyltriphenylammonium iodide and phenyltrimethylammonium iodide, methyltributylammonium hydroxide, methyltriethylammonium hydroxide, tetramethylammonium hydroxide, tetraethylammonium hydroxide, tetrapropylammonium hydroxide, tetrabutylammonium hydroxide, tetrapentylammonium hydroxide, tetrahexylammonium hydroxide, tetraoctylammonium hydroxide, tetradecylammonium hydroxide, tetradecyltrihexylammonium hydroxide, tetraoctadecylammonium hydroxide, benzyltrimethylammonium hydroxide, benzyltriethylammonium hydroxide, trimethylphenylammonium hydroxide, triethylmethylammonium hydroxide, trimethylvinylammonium hydroxide, tetramethylammonium fluoride, tetraethylammonium fluoride, tetrabutylammonium fluoride, tetraoctylammonium fluoride and benzyltrimethylammonium fluoride. These catalysts may be added alone or in mixtures. Preference is given to using tetraethylammonium benzoate and tetrabutylammonium hydroxide.

As catalyst D) it is also possible to use metal complexes with chelate ligands. The chelate ligands are organic compounds having at least two functional groups which are able to coordinate to metal atoms or metal ions. Use may be made, for example, of the aluminium- and zirconium-chelate complexes, as described in U.S. Pat. No. 4,772,672 A, for example, as catalyst. Preferred metal chelates are chelate based on zinc, lithium, tin, aluminium, zirconium, titanium and/or boron, for example aluminium ethyl acetoacetate, zirconium ethyl acetoacetate, zinc acetylacetonate, lithium acetylacetonate and tin acetylacetonate, alone or in mixtures. Preference is given to using zinc acetylacetonate.

Useful catalysts D) are also quaternary ammonium acetylacetonates or quaternary phosphonium acetylacetonates.

Examples of such catalysts are tetramethylammonium acetylacetonate, tetraethylammonium acetylacetonate, tetrapropylammonium acetylacetonate, tetrabutylammonium acetylacetonate, benzyltrimethylammonium acetylacetonate, benzyltriethylammonium acetylacetonate, tetramethylphosphonium acetylacetonate, tetraethylphosphonium acetylacetonate, tetrapropylphosphonium acetylacetonate, tetrabutylphosphonium acetylacetonate, benzyltrimethylphosphonium acetylacetonate, benzyltriethylphosphonium acetylacetonate. Particular preference is given to using tetraethylammonium acetylacetonate and tetrabutylammonium acetylacetonate. It is of course also possible to use mixtures of such catalysts, Further suitable as catalyst D) are aluminium, zirconium, titanium and/or boron alkoxides and/or esters thereof.

Also suitable as catalysts are basic substances, for example guanidines and amidines and tertiary amines. Examples of these are tetramethylguanidine, diazabicycloundecene (DBU), diazabicyclononene (DEN), and diazabicyclooctane (DABCO).

As catalyst D) it is also possible to catalyse the urethane reaction using catalysts which have proved their worth within the field of PU technology, examples being organic Sn(IV), Sn(II), Zn and Bi compounds, or organometallic catalysts, for example dibutyltin dilaurate, tin octoate, bismuth neodecanoate, or tertiary amines, for example 1,4-diazabicyclo[2.2.2]octane. Catalysts of these kinds for urethane reactions are used in accordance with the invention, however, only in blends with other catalysts of the invention.

As catalyst D) it is also possible to use a phosphorus-containing catalyst, preferably a phosphorus- and nitrogen-containing catalyst. Mixtures of two or more different catalysts may also be used here. Examples of suitable phosphorus-containing catalysts are substituted phosphonic diesters and diphosphonic diesters, preferably from the group consisting of acyclic phosphonic diesters, cyclic phosphonic diesters, acyclic diphosphonic diesters and cyclic diphosphonic diesters. Catalysts of these kinds are described in DE-A 102005045228, for example.

As catalyst D) it is also possible with preference to use an amine-blocked phosphoric ester and with particular preference amine-blocked ethylhexyl phosphate and amine-blocked phenyl phosphate. Examples of amines with which the phosphoric esters are blocked are especially tertiary amines, for example triethylamine. Particularly preferred for use for blocking the phosphoric esters are tertiary amines which exhibit high catalyst activity at curing temperatures of 100 to 160° C. Certain amine-blocked phosphoric acid catalysts are also available commercially (e.g. Nacure products from King Industries). An example of a particularly suitable catalyst is that based on an amine-blocked partial ester of phosphoric acid, under the designation Nacure 4167 from King Industries.

Also possible for use as catalyst D) are organic sulphonic acids in non-blocked or blocked form. A suitable sulphonic acid is in principle any organic sulphonic acid, preference being given to p-toluenesulphonic acid and dodecylbenzenesulphonic acid. For coating systems which crosslink thermally, i.e. above 100° C., these sulphonic acids, in accordance with the invention, may also be employed preferably in amine-neutralized form. Also possible for use in accordance with the invention are latent, non-Ionogenic sulphonic acid derivatives which release sulphonic acids only at above 100° C., such as adducts of sulphonic acids with epoxide-containing components, for example, as described in DE A 23 56768.

Salts of trifluoromethanesulphonic acid (triflates) as well are suitable sulphonic acid-based catalysts.

The catalyst D) in the coating compositions of the invention may consist solely of the abovementioned alternatives, although any desired mixtures of the catalysts may also be used.

The coating composition of the invention may further comprise auxiliaries and/or adjuvants E) that are known within coatings technology, such as stabilizers, including light stabilizers, catalysts, additional crosslinkers, fillers, pigments, flow control agents or rheological assistants, such as "sag control agents", for example, microgels or pyrogenic silicon dioxide or else nanoparticles as described, for example in EP 1204701 B1, in typical concentrations. Component E) may further comprise additional crosslinkers as known within coatings chemistry, which are used, for example, in the form of melamine resins, benzoguanamine resins, carbamate-functional components or blocked polyisocyanates. If necessary, inorganic or organic colour and/or effect pigments customary in coating technology may also be incorporated in component E) of the coating compositions of the invention.

In one preferred embodiment the coating composition of the invention is a pigment-free system, i.e. a clearcoat system. Component E) in this case may be included in the coating composition of the invention preferably in an amount of 0.5 up to 8 weight percent, more preferably 1 to 6 weight percent, based on the sum of the components A), B) and C). Component E) is present, for example, in an amount of 6%, based on the sum of the components A), B) and C), when the coating composition, i.e. the sum of components A), B), C), D), E) and F), has a total weight of 110 g, with the sum of components A), B) and C) here being 100 g, the amount of E) being 6 g, and the amount of D) and F) being in each case 2 g.

In another preferred embodiment, the coating composition of the invention is a coloured coating system. Pigments and fillers as component E) may in this case be included in the coating composition of the invention in an amount from 10 to 200 weight percent, based on the sum of the components A), B), and C), For example, component E) is present in an amount of 200 weight percent, based on the sum of the components A), B) and C), tithe coating composition, i.e. the sum of the components A), B), C), D), E) and F), has a total weight of 110 g, with the sum of components A), B) and C) being 30 g, the amount of E) being 60 g and the amount of D) and F) being 10 g in each case.

The coating composition of the invention may further comprise organic solvents as component F). Suitable solvents are, for example, ketones, alcohols, esters, or aromatics.

Component F) is included in the coating composition of the invention preferably in amounts from 20 up to 150 weight percent, more preferably 30 to 60 weight percent, based on the sum of the components A), B) and C).

The respective fractions of the components A), B), C), D), E) and F) are selected in their entirety such that the weight fractions add up to 100 weight percent.

A further preferred embodiment is a coating composition of the invention as follows:
coating composition comprising
A) 10-99 wt % of at least one allophanate-containing compound having the formula 1:

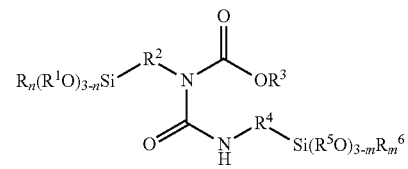

where R, $R^1$-$R^6$ are each independently identical or different hydrocarbyl radicals having 1-8 carbon atoms, which may be branched or cyclic, or else may be integrated together to form a cyclic system, and m and n are each independently 0-2,
B) 1-90 wt % of at least one binder, preferably a hydroxyl-containing or amine-containing binder,
C) 0-50 wt % of at least one aliphatic or cycloaliphatic polyisocyanate having an NCO functionality of at least 2, preferably 2.8 to 6, D) 0-5 wt % of at least one catalyst,
E) 0-50 wt % of auxiliaries and/or additive,
where the components add up to 100 wt %,
F) optionally solvents.

The coating compositions of the invention are produced by mixing of the components described above. The mixing may take place by means of mixers known to the skilled person, for example batchwise in stirred containers, dissolvers, bead mills, roll mills, etc., or else continuously using static mixers, for example.

The present invention is more particularly described by the following non-limiting examples from which further features, embodiments, aspects and advantages of the present invention may be discerned.

Also provided by the invention is the use of the coating compositions of the invention in paint compositions for metal, plastic, glass, wood, MDF (Middle Density Fibreboard) or leather substrates or other heat-resistant substrates.

Also provided by the invention is the use of the coating compositions of the invention in adhesive compositions for bonds of metal, plastic, glass, wood, MDF or leather substrates or other heat-resistant substrates.

Likewise provided by the invention are metal-coating compositions, more particularly for car bodies, motorcycles and pedal cycles, parts of buildings and household appliances, wood-coating compositions, MDF coatings, glass-coating compositions, leather-coating compositions and plastic-coating compositions.

The present invention is more particularly described by the following non-limiting examples from which further features, embodiments, aspects and advantages of the present invention may be discerned.

EXAMPLES

1) Preparation of the Monoallophanates
a)
236 g (1 mol) of trimethoxysilylpropylmethyl carbamate (Evonik Industries AG) and 205 g of isocyanatopropyltrimethoxysilane (Evonik Industries AG) are mixed with one another and heated to 175° C. for 2 h. Thereafter, the starting materials are removed at 100° C. and 0.3 mbar by means of a short-path distillation. This leaves 183 g (41.5%) of a clean, water-clear liquid, 013-NMR in CDCl$_3$ (ppm): 156.9 (1); 154.4 (1); 53.5 (1); 50.5 (10); 46.3 (1); 43.2 (1); 23.2 (1); 22.6 (1); 6.7 (1); 6.5 (1).

Viscosity is about 200 mPas and hence is very low.
b)
236 g (1 mol) of trimethoxysilylpropylmethyl carbamate (Evonik Industries AG), 205 g of isocyanatopropyltrimethoxysilane (Evonik Industries AG) and 0.4 g of tin(II) chloride are mixed with one another and heated to 150° C. for 1 h. Thereafter, the starting materials are removed at 90° C. and 0.3 mbar by means of a short-path distillation. This leaves 339 g (76.9%) of a clean, water-clear liquid, (for NMR see above)
c)
236 g (1 mol) of trimethoxysilylpropylmethyl carbamate (Evonik Industries AG), 205 g of isocyanatopropyltrimethoxysilane (Evonik Industries AG) and 1 g of iron(III) acetylacetonate are mixed with one another and heated to 90° C. for 3 h. Thereafter, the starting materials are removed at 90° C. and 0.3 mbar by means of a short-path distillation. This leaves 184 g (41.5%) of a clean, water-clear liquid. (for NMR see above)

2) Inventive coating composition
Formulation:
44.5 g of Setalux 1760 (OH-functional acrylate, Nuplex industries) and 30 g of inventive product a) are mixed with 25 g of butyl acetate/xylene (1:1), and 0.5 g of catalyst (VESTANAT EP-CAT 11, Evonik Industries AG) is added. This mixture is coated onto a steel sheet with a 120 μm spiral coating bar and baked at 140° C. for 22 min. The coating (layer thickness 30 μm) has a pendulum hardness of 176 s and a chemical resistance of >150 MEK twin strokes. It is thus fully cured.

Scratch Resistance:
The starting gloss is 86 scale divisions (SD) (20°) After the brush test, the gloss has dropped to 84 SD. The Crockmeter test leads to a gloss of 83 SD. The loss of gloss is thus 2 or 3 SD and hence the scratch resistance is excellent.

Evaluation: loss of gloss resulting from scratches 0-9 SD excellent, 10-20 very good, 21-34 good, 35-44 average, >45 poor By comparison, commercial 2-pack PUR paints based on Setalux 1760 have a loss of gloss of about 30 SD.

Brush Test (Wet):
Instrument: U 1 Serial no. 003, manufacturer: BASF L+F, built: 1993 The paint surface is damaged with a screen fabric (nylon screen fabric no. 11, mesh size 25 μm) under a weight (2 kg). The screen fabric and the paint surface are wetted copiously with a detergent solution (0.25% Persil solution in water), The test panel is moved in backward and forward strokes under the screen fabric with the aid of a motor drive. The gloss is measured before and after the test.

Crockmeter Test (Dry)
Instrument: U 1 Serial no. 003, manufacturer: BASF L+F, built: 1993
The paint surface is damaged with a fabric (3M 281Q WetODry Polishing Paper) under a weight (920 g). The test panel is moved in backward and forward strokes under the fabric with the aid of a motor drive.

The invention claimed is:
1. A coating composition, comprising:
A) at least one allophanate-containing compound having the formula (1):

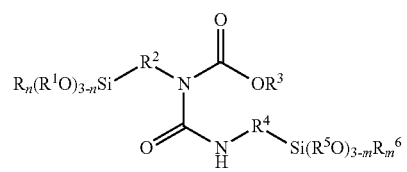

wherein
R, $R^1$-$R^6$ are each independently identical or different hydrocarbyl radicals having 1-8 carbon atoms, which may be branched or cyclic, or else may be integrated together to form a cyclic system, and
m and n are each independently 0-2,
B) at least one binder,
C) optionally at least one aliphatic or cycloaliphatic polyisocyanate having an NCO functionality of at least 2,
D) optionally at least one catalyst,
E) optionally at least one auxiliary and/or additive,
F) optionally at least one solvent.

2. The coating composition according to claim 1, comprising:

A) 10-99 wt % of at least one allophanate-containing compound having the formula (1):

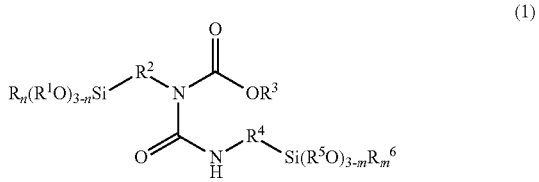

wherein
R, $R^1$-$R^6$ are each independently identical or different hydrocarbyl radicals having 1-8 carbon atoms, which may be branched or cyclic, or else may be integrated together to form a cyclic system, and
m and n are each independently 0-2,
B) 1-90 wt % of at least one binder,
C) 0-50 wt % of at least one aliphatic or cycloaliphatic polyisocyanate having an NCO functionality of at least 2,
D) 0-5 wt % of at least one catalyst,
E) 0-50 wt % of at least one auxiliary and/or additive,
F) optionally at least one solvent,
where components A)-F) add up to 100 wt. %.

3. The coating composition according to claim 1, wherein m and n are each 0,
$R^1$ and $R^5$ are each methyl or ethyl, and
$R^2$ and $R^4$ are each methylene or propylene.

4. The coating composition according to claim 1, wherein m and n are each 0,
$R^1$=$R^5$=methyl and $R^2$=$R^4$=propylene.

5. The coating composition according to claim 1, wherein binder B) comprises at least one member selected from the group consisting of a hydroxyl-containing binder and an amine-containing binder.

6. The coating composition according to claim 1, wherein binder B) comprises at least one member selected from the group consisting of a hydroxyl-containing polyester having an OH number of 20 to 500 mg KOH/g and a mean molar mass of 250 to 6000 g/mol, a hydroxyl-containing polyether having an OH number of 20 to 500 mg KOH/g and a mean molar mass of 250 to 6000 g/mol, a hydroxyl-containing polyacrylate having an OH number of 20 to 500 mg KOH/g and a mean molar mass of 250 to 6000 g/mol, a hydroxyl-containing polycarbonate having an OH number of 20 to 500 mg KOH/g and a mean molar mass of 250 to 6000 g/mol, and a hydroxyl-containing polyurethane having an OH number of 20 to 500 mg KOH/g and a mean molar mass of 250 to 6000 g/mol.

7. The coating composition according to claim 1, wherein binder B) comprises at least one member selected from the group consisting of a hydroxyl-containing polyester having an OH number of 20 to 500 mg KOH/g and a mean molar mass of 250 to 6000 g/mol and a hydroxyl-containing polyacrylate having an OH number of 20 to 500 mg KOH/g and a mean molar mass of 250 to 6000 g/mol.

8. The coating composition according to claim 1, wherein binder B) comprises at least one adduct of an isocyanatotrialkoxysilane and a mono- or polyhydric alcohol.

9. The coating composition according to claim 1, wherein binder B) comprises at least one member selected from the group consisting of a derivative of a hydroxyl-containing polyether with isocyanatopropyltrialkoxysilane, a derivative of a polyester with isocyanatopropyltrialkoxysilane, a derivative of a polycarbonatediol with isocyanatopropyltrialkoxysilane, and a derivative of a polyacrylate with isocyanatopropyltrialkoxysilane.

10. The coating composition according to claim 1, wherein binder B) comprises at least one member selected from the group consisting of aminopropyltriethoxysilane, aminomethyltrimethoxysilane, and aminomethyltriethoxysilane.

11. The coating composition according to claim 1, wherein component C) is present and is at least one member selected from the group consisting of isophorone diisocyanate (IPDI), hexamethylene diisocyanate (HDI), diisocyanatodicyclohexylmethane (H12MDI), 2-methylpentane diisocyanate (MPDI), 2,2,4-trimethylhexamethylene diisocyanate/2,4,4-trimethylhexamethylene diisocyanate (TMDI), and norbornane diisocyanate (NBDI).

12. The coating composition according to claim 1, wherein component C) is present and is at least one member selected from the group consisting of isophorone diisocyanate (IPDI), hexamethylene diisocyanate (HDI), 2,2,4-trimethylhexamethylene diisocyanate/2,4,4-trimethylhexamethylene diisocyanate (TMDI) and diisocyanatodicyclohexylmethane (H12MDI).

13. The coating composition according to claim 1, wherein component C) is present and comprises at least one isocyanurate.

14. The coating composition according to claim 1, wherein component D) is present and comprises at least one member selected from the group consisting of a metal carboxylate, a tert-amine, an amidine, a guanidine, a quaternary ammonium salt, a tetraalkylammonium salt, a quaternary phosphonium salt, a metal acetylacetonate, a quaternary ammonium acetylacetonate, and a quaternary phosphonium acetylacetonate.

15. The coating composition according to claim 1, wherein component E) is present and comprises at least one member selected from the group consisting of a stabilizer, a light stabilizer, a catalyst, an additional crosslinker, a filler, a pigment, a levelling agent, and a rheology aid.

16. A process for producing the coating composition according to claim 1, the process comprising:
mixing components A) and B), and, when present, any or all of components C), D), E), and F).

17. A paint composition, an adhesive composition, or a metal coating composition, which comprises:
the coating composition according to claim 1.

* * * * *